United States Patent [19]

Friebe et al.

[11] 4,288,442
[45] Sep. 8, 1981

[54] INHIBITING ADRENERGIC β-RECEPTORS WITH PIPERIDINOPROPYL DERIVATIVES

[75] Inventors: Walter-Gunar Friebe, Darmstadt; Helmut Michel, Mannheim; Carl H. Ross, Viernheim; Fritz Wiedemann, Weinheim-Lützelsachsen; Gisbert Sponer, Hemsbach; Wolfgang Schaumann, Heidelberg, all of Fed. Rep. of Germany

[73] Assignee: Boehringer Mannheim GmbH, Postfach, Fed. Rep. of Germany

[21] Appl. No.: 117,172

[22] Filed: Jan. 31, 1980

[30] Foreign Application Priority Data

Feb. 16, 1979 [DE] Fed. Rep. of Germany ....... 2905876

[51] Int. Cl.³ ................. A61K 31/445; C07D 401/12; C07D 401/14
[52] U.S. Cl. ..................................... 424/267; 424/251; 544/298; 544/316; 544/319; 546/197; 546/199; 546/200; 546/201; 546/208; 546/233
[58] Field of Search ............... 546/199, 200, 201, 197; 544/316, 319, 298; 424/267, 251

[56] References Cited

U.S. PATENT DOCUMENTS

| | | | |
|---|---|---|---|
| 4,110,333 | 8/1978 | Vandenberk et al. | 546/199 X |
| 4,144,344 | 3/1979 | Eichenberger et al. | 546/201 X |
| 4,146,630 | 3/1979 | Kampe et al. | 546/201 X |
| 4,200,641 | 4/1980 | Vandenberk et al. | 546/199 X |

FOREIGN PATENT DOCUMENTS 2550001 5/1977 Fed. Rep. of Germany .

Primary Examiner—Richard A. Schwartz

Attorney, Agent, or Firm—Sprung, Felfe, Horn, Lynch & Kramer

[57] ABSTRACT

A piperidinopropyl derivative of the formula

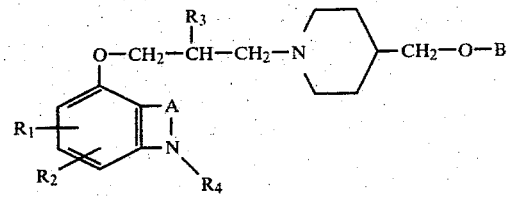

in which
 $R_1$ and $R_2$ each independently is hydrogen or a lower alkyl radical, or together are an alkylene radical,
 $R_3$ is hydrogen, hydroxy, or acyloxy,
 $R_4$ is hydrogen or formyl,
 A together with the adjacent benzene ring and N-$R_4$ forms a benzimidazolin-2-one, benzimidazoline-2-thione, oxindole, indazole carbazole, benztriazole, benzimidazole, indoline or indole moiety, and
 B is a heterocyclic radical or, under certain circumstances, a phenyl radical, either of which is optionally substituted by halogen, hydroxy, lower alkyl, hydroxy-lower alkyl, carboxamido-lower alkyl, lower alkoxy, amino, carboxamido, lower alkylcarbonylamino, acyl or lower alkylsulphonylamino, or a pharmacologically acceptable salt thereof. The compounds inhibit adrenergic β-receptors and lower blood pressure.

10 Claims, No Drawings

INHIBITING ADRENERGIC β-RECEPTORS WITH PIPERIDINOPROPYL DERIVATIVES

The present invention is concerned with new piperidinopropyl derivatives, with the preparation thereof and with pharmaceutical compositions containing them.

The new piperidinopropyl derivatives according to the present invention are compounds of the general formula:

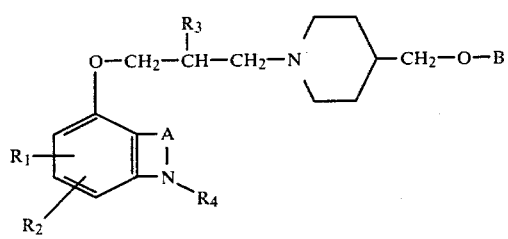

wherein $R_1$ and $R_2$, which can be the same or different, are hydrogen atoms or lower alkyl radicals or together represent an alkylene radical, $R_3$ is a hydrogen atom or $-O-R_5$, $R_5$ being a hydrogen atom or an acyl radical, $R_4$ is a hydrogen atom or a formyl radical, A is an $-X_1=Y_1-$ grouping, in which $X_1$ and $Y_1$, which can be the same or different, are nitrogen atoms or $-C(R_6)=$, in which $R_6$ is a hydrogen atom, a lower alkyl radical optionally substituted by $-O-R_5$, a carboxyl or an alkoxycarbonyl radical, or A is an $-X_2-Y_2-$ grouping, in which $X_2$ is $-CH_2-$ or $-N(R_7)-$, in which $R_7$ is a hydrogen atom or a lower alkyl radical, and $Y_2$ is $-CH_2-$ or $-C(=Z)-$, in which Z is an oxygen or sulphur atom, or A is a $-CR_8=CR_9$ grouping, in which $R_8$ and $R_9$ together represent a $-CH=CH-CH=CH-$ bridge, with the proviso that $Y_1$ or $Y_2$ is connected to $>N-R_4$ in general formula (I), and B is a heterocyclic radical or, if A represents $-X_2-Y_2-$ or $-CR_8=CR_9-$, may also be a phenyl radical, which are optionally substituted one or more times by halogen, hydroxyl or lower alkyl, which optionally carries a hydroxyl group or a carboxamido substituent, by a lower alkoxy, amino, carboxamido, lower alkylcarbonylamino, acyl or lower alkylsulphonylamino radical; and the pharmacologically acceptable salts thereof.

Since, when $R_3$ is not a hydrogen atom, the compounds of general formula (I) contain an asymmetric carbon atom, they can be present in optically-active form or as a racemic mixture. Consequently, the present invention includes not only the racemic forms but also the optically-active isomers.

The acyl radicals which can possibly be represented by $R_5$ and the substituent on B can be acid residues of straight-chained or branched aliphatic carboxylic acids containing 2 to 6 carbon atoms or of aromatic carboxylic acids optionally substituted by halogen, lower alkyl or lower alkoxy. The acetyl, pivaloyl and benzoyl radicals are preferred.

The lower alkyl and alkoxy radicals in the definitions of $R_1$, $R_2$, $R_5$, $R_6$ and $R_7$ can be straight-chained or branched and contain up to 6 and preferably up to 4 carbon atoms, the methyl, propyl, tert.-butyl, methoxy, ethoxy, propoxy and n-butoxy radicals being preferred.

The alkylene radical which can possibly be formed by $R_1$ and $R_2$ together can contain 2 to 4 carbon atoms.

Halogen according to the present invention is to be understood to be fluorine, chlorine, bromine or iodine, fluorine, chlorine and bromine being preferred.

A heterocyclic radical B is to be understood to be a monocyclic radical, for example, a pyridyl or pyrimidyl radical, or a bicyclic radical, for example a benzimidazolinonyl, benzimidazolinyl, benztriazolyl, indazoyl or benzodioxolanyl radical, or a tricyclic radical, for example, a carbazolyl radical, with one, two or three hetero atoms. The pyridyl, pyrimidyl, benzimidazolinonyl and benzodioxolanyl radicals are preferred.

Heterocyclic radicals which the benzene ring forms with A are preferably derived from benzimidazolin-2-one, benzimidazoline-2-thione, oxindole, indazole, carbazole, benztriazole, benzimidazole, indoline or indole.

The compounds of general formula (I), as well as their pharmacologically acceptable salts, inhibit adrenergic β-receptors and, at the same time, lower the blood pressure to a large extent. Therefore, they are suitable for treatment or prophylaxis in cases of cardiac and circulatory diseases.

U.S. Pat. No. 4,146,630 describes compounds of similar structure and action. By changing the heterocyclic phenolic parts of the molecule, as well as by introducing heterocycles into the side chain, a surprising improvement of the activity is achieved.

The new compounds of general formula (I) can be prepared, for example, by one of the following processes:

(a) a compound of the general formula:

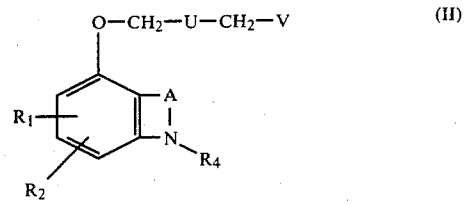

is reacted with a compound of the general formula:

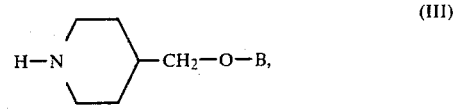

wherein $R_1$, $R_2$, $R_4$, A and B have the same meanings as above, V is a reactive residue and U is $>C=O$, $>CH-R_3$ or $>CH-O-E$, in which $R_3$ has the same meaning as above and E, together with V, represents a valency bond, followed by reduction when U is $>C=O$; or (b) a compound of the general formula:

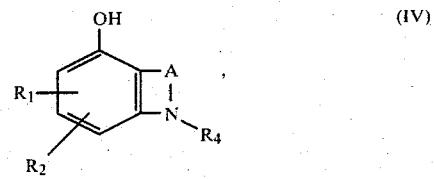

is reacted with a compound of the general formula:

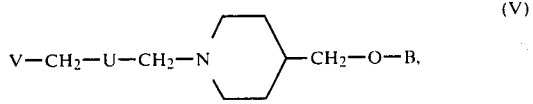

in which $R_1$, $R_2$, $R_4$, A, B, U and V have the same meanings as above and, when U is $>C=O$, followed by reduction; or (c) when A in general formula (I) is to be $-X_1=Y_1-$, a compound of the general formula:

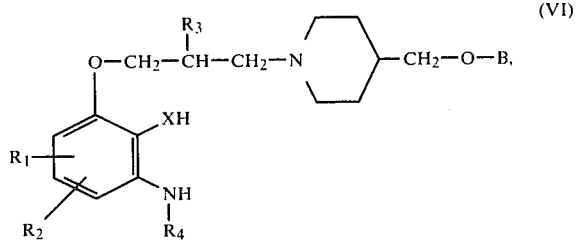

in which $R_1$, $R_2$, $R_3$, $R_4$ and B have the same meanings as above and X is $HX_1$, is reacted with a compound of the general formula:

in which $Y_1$ has the same meaning as above, $L_1$ is a hydrogen atom, a hydroxyl group or a reactive residue T, $L_2$ is a hydrogen atom or a reactive residue T and $L_3$ is a hydrogen atom or, together with $L_2$, represents an oxygen atom; or, when A in general formula (I) is to be $-X_2-Y_2$, a compound of general formula (VI), in which X is $X_2$, is reacted with a compound of the general formula:

in which $L_1$ and $L_2$ have the same meanings as above and $L_2'$ is a hydrogen atom or a reactive residue T, followed in both cases by cyclization; or (d) a compound of the general formula:

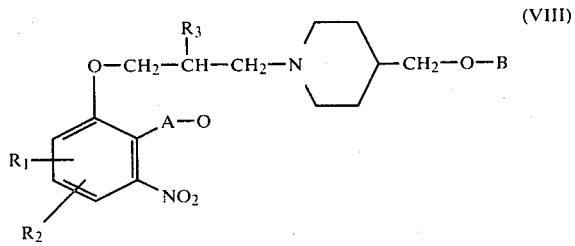

in which $R_1$, $R_2$, $R_3$, A and B have the same meanings as above and Q is a group which can be split off, is reduced and cyclized, whereafter compounds of general formula (I) in which $R_3$ is a hydroxyl group are, if desired, acylated, a substituent $R_6$ or a substituent in B is, if desired, converted into another substituent and, if desired, the compounds obtained of general formula (I) are converted into their pharmacologically acceptable salts.

Q, V and T in compounds of general formulae (II), (V), (VIIa), (VIIb) and (VIII) stand for all residues which can be nucleophilically substituted, examples of such residues including halogen atoms, preferably bromine or chlorine atoms, sulphonic acid esters, amino, imidazolyl, lower alkoxy and also mercapto groups.

The processes according to the present invention are preferably carried out in a solvent which is inert under the reaction conditions, for example, water, ethanol, dioxane or dimethylformamide, optionally in the presence of an acid-binding agent. The reaction can also be carried out, after mixing the reaction components, without the use of a solvent. The reaction is carried out by leaving the reaction mixture to stand at ambient temperature or by heating, optionally under an atmosphere of an inert gas.

The reaction of the compounds of general formula (IV) with compounds of general formula (V) according to process (b) is preferably carried out with the exclusion of oxygen and in the presence of an acid acceptor. However, it is also possible to use alkali metal salts of the hydroxyl compounds of general formula (IV).

When a $>C=O$ group is to be reduced, this can be carried out by catalytic hydrogenation with a noble metal or nickel catalyst or by means of a complex metal hydride, for example sodium borohydride.

Compounds of general formula (III) either described in published U.S. application Ser. No. 737,518, filed Nov. 1, 1976, now U.S. Pat. No. 4,243,807, and can be prepared by the processes described therein.

Compounds of general formula (IV) are known and can be prepared from known compounds analogously to processes (c) or (d).

Compounds of general formula (VI) are known from U.S. Pat. No. 4,146,630 and can be prepared by the processes described therein.

The compounds of general formula (VIIa) can be, for example, carboxylic acids, such as formic acid or acetic acid, carboxylic acid esters or carboxylic acid halides. Compounds of general formula (VIIb) can be, for example, phosgene, urea, N,N'-carbonyl-bis-imidazole, thiocarbonyl halides, thiourea or also xanthogenates. Compounds of general formula (VIIa) can also be prepared in situ in the reaction mixture from other compounds, for example from inorganic nitrite in aqueous mineral acid or from lower alkyl nitrous acid esters in organic solvents. Compounds of general formula (VIIb) can also be prepared in the reaction mixture, for example from carbon disulphide in alkaline solution.

Reductions such as are necessary for process (d) are preferably carried out with catalytically activated hydrogen.

The optional subsequent acylation of compounds of general formula (I), in which $R_3$ is a hydroxyl group, can be carried out in known manner by reaction with a reactive acid derivative, for example an acid halide, acid azide or acid anhydride, optionally in the presence of an acid-binding agent, for example pyridine, in a solvent, for example acetone, benzene or dimethylformamide, or also in excess acid.

One possible subsequent conversion of a substituent $R_6$ into a different substituent $R_6$ is, for example, the reduction of an alkoxycarbonyl radical to a hydroxymethyl radical, this reduction being carried out by generally known methods. A carboxylic acid ester is preferably reduced with a complex metal hydride, for example lithium aluminum hydride, in a neutral organic solvent, for example tetrahydrofuran.

One example of a subsequent conversion of a substituent in B is the conversion of an amino group into an alkylcarbonylamido or alkylsulphonylamido radical. These reactions can also be carried out by known methods with conventional acylation agents, for example carboxylic acid anhydrides, carboxylic acid chlorides or alkylsulphonic acid chlorides.

The compounds of general formula (I) according to the present invention can be obtained in the form of a racemic mixture. The separation of the racemate into the optically-active form is carried out by known methods via the diastereomeric salts with active acids, for example tartaric acid, malic acid or camphorsulphonic acid.

The new compounds of general formula (I) are, under the reaction conditions of the described processes, usually obtained as acid-addition salts, for example as hydrochlorides, and can be readily converted into the free bases by known methods.

For the conversion of compounds of general formula (I) into their pharmacologically acceptable salts, these are reacted, preferably in an organic solvent, with an equivalent amount of an inorganic or organic acid, for example, hydrochloric acid, hydrobromic acid, phosphoric acid, sulphuric acid, acetic acid, citric acid or maleic acid.

For the preparation of pharmaceutical compositions, the compounds of general formula (I) are mixed in the usual way with appropriate pharmaceutical carriers, aroma, flavoring and coloring materials and formed, for example, into tablets or dragees or, with the addition of appropriate adjuvants, are suspended or dissolved in water or in an oil, for example olive oil.

The new compounds (I) according to the present invention and the salts thereof can be administered enterally or parenterally in liquid or solid form. As injection medium, it is preferable to use water which contains the additives usual in the case of injection solutions, such as stabilizing agents, solubilizing agents or buffers. Additives of this type include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The dosage administered depends upon the age, the state of health and the weight of the recipient, the extent of the disease, the nature of further treatments possibly carried out at the same time, the frequency of the treatment and the nature of the desired action. Normally, the daily dose of the active compounds is 0.1 to 50 mg./kg. of body weight. Usually, 0.5 to 40 and preferably 1.0 to 20 mg./kg./day, in one or more administrations, are effective in order to achieve the desired results.

Apart from the compounds mentioned in the following examples, the following compound is also preferred according to the present invention:

4-[2-hydroxy-3-(4-phenoxymethylpiperidino)-propoxy]-6,7-cyclopenteno-2-benzimidazolinone.

The following examples, which are given for the purpose of illustrating the present invention, describe some of the numerous possible process variants which can be used for the synthesis of the new compounds according to the present invention:

EXAMPLE 1

4-[2-Hydroxy-3-(4-phenoxymethylpiperidino)-propoxy]-2-benzimidazolinone hydrochloride 23.0 g. 2,3-Diamino-1-[2-hydroxy-3-(4-phenoxymethylpiperidino)-propoxy]-benzene trihydrochloride are dissolved in 600 ml. water and phosgene is passed into the solution for 40 minutes. The crystals obtained are filtered off with suction, taken up in 500 ml. hot ethanol, treated with active charcoal and precipitated out with 2.5 liters diethyl ether. After again recrystallizing from ethanol/water (1:1 v/v), there are obtained 9.1 g. (43% of theory) 4-[2-hydroxy-3-(4-phenoxymethylpiperidino)-propoxy]-2-benzimidazolinone hydrochloride; m.p. 144°–146° C.

The following compounds are obtained in an analogous manner:

| designation | Yield % of theory | melting point °C. (solvent) |
|---|---|---|
| (a) 4-{2-hydroxy-3-[4-(2-methoxyphenoxymethyl)-piperidino]-propoxy}-2-benzimidazolinone hydrochloride from 2,3-diamino-1-{2-hydroxy-3-[4-(2-methoxyphenoxymethyl)-piperidino]-propoxy}-benzene trihydrochloride and phosgene | 42 | 162–164 (methanol) |
| (b) 4-{2-hydroxy-3-[4-(3-methylphenoxymethyl)-piperidino]-propoxy}-2-benzimidazolinone hydrochloride from 2,3-diamino-1-{2-hydroxy-3-[4-(3-methylphenoxymethyl)-piperidino]-propoxy}-benzene trihydrochloride and phosgene | 40 | 227–229 (methanol) |
| (c) 4-[3-(4-phenoxymethylpiperidino)-propoxy]-2-benzimidazolinone hydrochloride from 2,3-diamino-1-[3-(4-phenoxymethylpiperidino)-propoxy]-benzene trihydrochloride and phosgene | 48 | 257–258 (methanol) |
| (d) 4-[2-hydroxy-3-(4-phenoxymethylpiperidino)-propoxy]-6-methyl-2-benzimidazolinone hydrochloride from 2,3-diamino-1-[2-hydroxy-3-(4-phenoxymethylpiperidino)-propoxy]-5-methyl-benzene trihydrochloride and phosgene | 31 | 245–247 (ethanol) |
| (e) 4-[2-hydroxy-3-(4-phenoxymethyl)-piperidino]-6-tert.-butyl-2-benzimidazolinone hydrochloride from 2,3-diamino-1-[2-hydroxy-3-(4-phenoxymethylpiperidino)-propoxy]-5-tert.-butyl-benzene trihydrochloride and phosgene | 18 | 261–262 (acetone) |
| (f) 4-{2-hydroxy-3-[4-(2-pyridyloxymethyl)-piperidino]-propoxy}-2-benzimidazolinone hydrochloride from 2,3-diamino-1-{2-hydroxy-3-[4- | 62 | 195–197 (ethanol/ |

-continued

| designation | Yield % of theory | melting point °C. (solvent) |
|---|---|---|
| (2-pyridyloxymethyl)-piperidino]-propoxy}-benzene trihydrochloride and phosgene | | methanol) |
| (g) 4-{2-hydroxy-3-[4-(4-2-benzimidazolinonyloxymethyl)-piperidino]-propoxy}-2-benzimidazolinone hydrochloride from 2,3-diamino-1-{2-hydroxy-3-[4-(4-2-benzimidazolinonyloxymethyl)-piperidino]-propoxy}-benzene trihydrochloride and phosgene | 20 | 223–226 (methanol/water) |
| (h) 4-{2-hydroxy-3-[4-(4-methyl-(2)-pyrimidyloxymethyl)-piperidino]-propoxy}-2-benzimidazolinone hydrochloride from 2,3-diamino-1-{2-hydroxy-3-[4-(4-methyl-(2)-pyrimidyloxymethyl)-piperidino]-propoxy}-benzene trihydrochloride and phosgene | 25 | 152–155 (ethanol/methanol) |

EXAMPLE 2

4-[2-Pivaloyloxy-3-(4-phenoxymethylpiperidino)-propoxy]-2-benzimidazolinone hydrochloride 5.00 g. 4-[2-Hydroxy-3-(4-phenoxymethyl-piperidino)propoxy]-2-benzimidazolinone (preparation: see Example 1) are added to 31.5 g. molten pivalic acid and then mixed with 6.28 g. pivalic anhydride. The reaction mixture is stirred for 5 days at ambient temperature, then poured into 100 ml. ice water, neutralized with dilute aqueous ammonia solution (1:10 v/v) and extracted with dichloromethane, whereafter the extract is dried over anhydrous sodium sulphate and evaporated. The residue is washed with diethyl ether, dissolved in ethanol and mixed with 2 N hydrochloric acid. After evaporation, the residue obtained is recrystallized from 20 ml. ethanol. There are obtained 3.65 g. (56% of theory) 4-[2-pivaloyloxy-3-(4-phenoxymethyl-piperidino)-propoxy]-2-benzimidazolinone hydrochloride; m.p. 168°–170° C.

EXAMPLE 3

4-[2-Hydroxy-3-(4-phenoxymethylpiperidino)-propoxy]-6,7-dimethyl-2-benzimidazolinone hydrochloride 2,3-Diamino-4,5-dimethyl-1-[2-hydroxy-3-(4-phenoxymethylpiperidino)-propoxy]-benzene trihydrochloride is reacted with phosgene analogously to Example 1 to give 4-[2-hydroxy-3-(4-phenoxymethylpiperidino)-propoxy]-6,7-dimethyl-2-benzimidazolinone hydrochloride in a yield of 24% of theory; m.p. 273°–275° C.

The 2,3-diamino-4,5-dimethyl-1-[2-hydroxy-3-(4-phenoxymethylpiperidino)-propoxy]-benzene trihydrochloride used as starting material can be prepared in the following manner:

15.9 g. 2-Amino-1-(2,3-epoxypropoxy)-4,5-dimethyl-3-nitrobenzene and 12.8 g. 4-phenoxymethylpiperidine are heated under reflux for 1.5 hours in 300 ml. ethanol. The solution is then cooled and added to 1.0 g. platinum oxide in 100 ml. ethanol and hydrogenated at ambient temperature. After filtration, the filtrate is acidified with dilute hydrochloric acid and then evaporated. The residue is taken up in aqueous ethanol, treated with active charcoal, filtered and the filtrate evaporated to give 28.4 g. (84% of theory) 2,3-diamino-4,5-dimethyl-1-[2-hydroxy-3-(4-phenoxymethylpiperidino)-propoxy]-benzene trihydrochloride; m.p. 144°–145° C.

The following compound is obtained in an analogous manner:

(a) 4-{2-hydroxy-3-[4-(4-carboxamidophenoxymethyl)-piperidino]-propoxy}-6,7-dimethyl-2-benzimidazolinone hydrochloride (m.p. 311°–313° C., after recrystallization from aqueous ethanol) in 29% yield from 2,3-diamino-1-{2-hydroxy-3-[4-(4-carboxamidophenoxymethyl)-piperidino]-propoxy}-4,5-dimethyl-benzene trihydrochloride and phosgene.

EXAMPLE 4

The following compounds are obtained in a manner analogous to that described in Example 1:

| designation | yield % of theory | melting point °C. (solvent) |
|---|---|---|
| (a) 4-[2-hydroxy-3-(4-phenoxymethylpiperidino)-propoxy]-7-methyl-2-benzimidazolinone hydrochloride from 2,3-diamino-1-[2-hydroxy-3-(4-phenoxymethylpiperidino)-propoxy]-4-methyl-benzene trihydrochloride and phosgene | 41 | 272–274 (methanol) |
| (b) 4-{2-hydroxy-3-[4-(2-methoxyphenoxymethyl)-piperidino]-propoxy}-7-methyl-2-benzimidazolinone hydrochloride from 2,3-diamino-1-{2-hydroxy-3-[4-(2-methoxyphenoxymethyl)-piperidino]-propoxy}-4-methyl-benzene trihydrochloride and phosgene | 13 | 139–141 (ethanol/ethyl acetate) |
| (c) 4-{2-hydroxy-3-[4-(2-methoxy-4-methylphenoxymethyl)-piperidino]-propoxy}-7-methyl-2-benzimidazolinone hydrochloride from 2,3-diamino-1-{2-hydroxy-3-[4-(2-methoxy-4-methylphenoxymethyl)-piperidino]-propoxy}-4-methyl-benzene trihydrochloride and phosgene | 17 | 248–250 (isopropanol/ethanol) |
| (d) 4-{2-hydroxy-3-[4-(4-carboxamidophenoxymethyl)-piperidino]-propoxy}-7-methyl-2-benzimidazolinone hydrochloride from 2,3-diamino-1-{2-hydroxy-3-[4-(4-carboxamidophenoxymethyl)-piperidino]-propoxy}-4-methyl-benzene trihydrochloride (amorphous) and phosgene | 37 | 294–296 (methanol/water) |

The 2,3-diamino-1-[2-hydroxy-3-(4-phenoxymethyl-piperidino)-propoxy]-4-methylbenzene trihydrochloride required as starting material for the preparation of the compound of Example (4a) is prepared in the following manner:

84.0 g. 1-(2,3-Epoxypropoxy)-4-methyl-2,3-dinitrobenzene and 63.2 g. 4-phenoxymethylpiperidine are boiled under reflux for 2.5 hours in 500 ml. ethanol. The reaction mixture is evaporated to dryness and the residue is taken up with 400 ml. boiling ethyl acetate and clarified with active charcoal. After filtration, the filtrate is mixed with 700 ml. boiling ligroin. There are obtained 103 g. (68% of theory) 1-[2-hydroxy-3-(4- phenoxymethylpiperidino)-propoxy]-4-methyl-2,3-dinitrobenzene; m.p. 127°–130° C.

73.2 g. of this dinitro compound, suspended in 500 ml. ethanol, are added to 1.0 g. platinum oxide in 150 ml. ethanol and hydrogenated at atmospheric pressure and ambient temperature. The suspension is dissolved by heating, filtered and the filtrate evaporated. The residue is taken up in 500 ml. hot ethanol, acidified with concentrated hydrochloric acid, clarified with active charcoal and then filtered and the filtrate evaporated to give 70 g. (89% of theory) of amorphous 2,3-diamino-1-[2-hydroxy-3-(4-phenoxymethylpiperidino)-propoxy]-4-methylbenzene trihydrochloride.

In an analogous manner, by the reaction of appropriately substituted piperidines with 1-(2,3-epoxypropoxy)-4-methyl-2,3-dinitrobenzene and subsequent hydrogenation, there are obtained the starting materials for the preparation of the compounds of Examples (4b) to (4d):

|  | Dinitro compound | m.p. °C. | o-phenylene-diamine derivative | m.p. °C. |
|---|---|---|---|---|
| (for 4b) | 1-{2-hydroxy-3-[4-(2-methoxyphenoxymethyl)-piperidino]-propoxy}-4-methyl-2,3-dinitrobenzene | 138–140 | 2,3-diamino-1-{2-hydroxy-3-[4-(2-methoxyphenoxymethyl)-piperidino]-propoxy}-benzene trihydrochloride | amorphous |
| (for 4c) | 1-{2-hydroxy-3-[4-(2-methoxy-4-methyl-phenoxymethyl)-piperidino]-propoxy}-4-methyl-2,3-dinitrobenzene | not isolated | 2,3-diamino-1-{2-hydroxy-3-[4-(2-methoxy-4-methyl-phenoxymethyl)-piperidino]-propoxy}-4-methylbenzene trihydrochloride | amorphous |
| (for 4d) | 1-{2-hydroxy-3-[4-(4-carboxamido-phenoxymethyl)-piperidino]-propoxy}-4-methyl-2,3-dinitrobenzene | 191–193 | 2,3-diamino-1-{2-hydroxy-3-[4-(4-carboxamido-phenoxymethyl)-piperidino]-propoxy}-4-methylbenzene trihydrochloride | amorphous |

EXAMPLE 5

4-{2-Hydroxy-3-[4-(2-methoxyphenoxymethyl)-piperidino]-propoxy}-2-benzimidazolinethione hydrochloride 6.1 g. of 2,3-Diamino-1-{2-hydroxy-3-[4-(2-methoxyphenoxymethyl)-piperidino]-propoxy}-benzene trihydrochloride are mixed with 12.0 ml. 1 M sodium methylate solution and evaporated to dryness. The residue is dissolved in 25 ml. ethanol and boiled under nitrogen for 6 hours with 2.1 g. potassium xanthogenate. The reaction mixture is filtered hot and the filtrate is clarified with active charcoal, filtered and the filtrate completely evaporated. After recrystallization of the residue from ethanol, there is obtained 1.26 g. (22% of theory) 4-{2-hydroxy-3-[4-(2-methoxyphenoxymethyl)-piperidino]-propoxy}-2-benzimidazolinone hydrochloride; m.p. 212°–215° C.

EXAMPLE 6

4-{2-Hydroxy-3-[4-(3-methylphenoxymethyl)-piperidino]-propoxy}-2-benzimidazolinone hydrochloride This compound is obtained, in a manner analogous to that described in Example 5, from 2,3-diamino-1-{2-hydroxy-3-[4-(3-methylphenoxymethyl)-piperidino]-propoxy}-benzene and potassium xanthogenate; m.p. 236°–237° C.

EXAMPLE 7

4-[2-Hydroxy-3-(4-phenoxymethylpiperidino)-propoxy]-7-methyl-3-propyl-2-benzimidazolinone In a manner analogous to that described in Example 1, from 3-amino-1-[2-hydroxy-3-(4-phenoxymethyl-piperidino)-propoxy]-4-methyl-2-propylaminobenzene trihydrochloride and phosgene, there is obtained, in a yield of 54% of theory, 4-[2-hydroxy-3-(4-phenoxymethylpiperidino)-propoxy]-7-methyl-3-propyl-2-benzimidazolinone; m.p. 234°–235° C.

The starting material required for Example 7 is prepared in the following manner:

15.0 g. 1-[2-hydroxy-3-(4-phenoxymethylpiperidino)-propoxy]-4-methyl-2,3-dinitrobenzene (see preparation of the starting material for Example (4a) are heated under reflux in 12 ml. n-propylamine for 3.5 hours. After cooling, there are isolated 8.8 g. (59% of theory) crystalline 1-[2-hydroxy-3-(4-phenoxymethylpiperidino)-propoxy]-4-methyl-2-propylamino-3-nitrobenzene; m.p. 91°–93° C. This compound is hydrogenated in the presence of platinum oxide to give the desired 3-amino-1-[2-hydroxy-3-(4-phenoxymethylpiperidino)-propoxy]-4-methyl-2-propylaminobenzene.

EXAMPLE 8

4-[2-Hydroxy-3-(4-phenoxymethylpiperidino)-propoxy]-oxindole acetate

A solution of 7.8 g. ethyl 2-[2-hydroxy-3-(4-phenoxymethylpiperidino)-propoxy]-6-nitrophenylacetate in 100 ml. methanol and 100 ml. acid is hydrogenated at ambient temperature and 1 bar hydrogen pressure in the presence of 10% palladium-charcoal. After filtering off the catalyst, the filtrate is distilled in a vacuum and the residue remaining behind is dissolved in water and filtered. By the addition of aqueous sodium carbonate solution, the base is precipitated out and then filtered off with suction. By dissolving the base in about 150 ml. ethyl acetate and 5 ml. acetic acid at boiling temperature, there are obtained, after cooling and suction filtration, 2.1 g. (27% of theory) 4-[2-hydroxy-3-(4-phenoxymethylpiperidino)-propoxy]-oxindole acetate; m.p. 125°–130° C.

The following compounds are obtained in a manner analogous to that described in Example 8:

|  | designation | yield % of theory | melting point °C. (solvent) |
|---|---|---|---|
| (a) | 4-{2-hydroxy-3-[4-(2-methoxy-phenoxymethyl)-piperidino]-propoxy}-oxindole acetate from ethyl 2-{2-hydroxy-3-[4-(2-methoxyphenoxymethyl)-piperidino]-propoxy}-6-nitrophenyl acetate | 37 | 114–118 (ethyl acetate) |
| (b) | 4-{2-hydroxy-3-[4-(3-methyl-phenoxymethyl)-piperidino]-propoxy}-oxindole acetate from ethyl 2-{2-hydroxy-3-[4-(3-methylphenoxymethyl)-piperidino]-propoxy}-6-nitrophenyl acetate | 28 | 161–162 (ethyl acetate) |
| (c) | 4-{2-hydroxy-3-[4-(4-hydroxy- | | |

-continued

| designation | yield % of theory | melting point °C. (solvent) |
|---|---|---|
| phenoxymethyl)-piperidino]-propoxy}-oxindole from ethyl 2-{2-hydroxy-3-[4-(4-benzyloxyphenoxymethyl)-piperidino]-propoxy}-6-nitrophenyl acetate | 38 | 192 (ethanol) |
| (d) 4-{2-hydroxy-3-[4-(2-chlorophenoxymethyl)-piperidino]-propoxy}-oxindole from ethyl 2-{2-hydroxy-3-[4-(2-chlorophenoxymethyl)-piperidino]-propoxy}-6-nitrophenyl acetate | 33 | 164–165 (methanol) |
| (e) 4-{2-hydroxy-3-[4-(3-hydroxymethyl-phenoxymethyl)-piperidino]-propoxy}-oxindole from ethyl 2-{2-hydroxy-3-[4-(3-hydroxymethyl-phenoxymethyl)-piperidino]-propoxy-}-6-nitrophenyl acetate | 27 | 152–154 (methanol) |
| (f) 4-{2-hydroxy-3-[4-(2-methyl-6-pyridoxymethyl)-piperidino]-propoxy}-oxindole from ethyl 2-{2-hydroxy-3-[4-(2-methyl-6-pyridoxymethyl)-piperidino]-propoxy}-6-nitrophenyl acetate | 17 | 165–167 (methanol) |
| (g) 4-{2-hydroxy-3-[4-(4-aminocarbonylmethylphenoxymethyl)-piperidino]-propoxy}-oxindole acetate from ethyl 2-{2-hydroxy-3-[4-(4-aminocarbonyl-methylphenoxymethyl)-piperidino]-propoxy}-6-nitrophenyl acetate | 46 | 173–175 (methanol) |

The ethyl 2-[2-hydroxy-3-(4-phenoxymethyl-piperidino)-propoxy]-6-nitrophenylacetate used as starting material for the preparation of the compound of Example 8 is obtained in the following manner:

2-Allyloxy-6-nitrotoluene 76.6 g. 2-Methyl-3-nitrophenol in 200 ml. methanol are mixed with 84.6 ml. allyl bromide and 375 ml. 2 N sodium methylate solution are added dropwise thereto. After standing for 18 hours at ambient temperature, the reaction mixture is distilled and the residue is taken up in water and diethyl ether. After evaporation of the ethereal phase, there are obtained 95.7 g. (99% of theory) 2-allyloxy-6-nitrotoluene.

Ethyl 2-allyloxy-6-nitrophenylpyruvate 0.625 mol Potassium tert.-butylate, 542 ml. diethyl oxalate and 95.7 g. 2-allyloxy-6-nitrotoluene are stirred for 3 hours at 60° C., then mixed with 1 N acetic acid and extracted with diethyl ether. The oxalic acid ester remaining behind in the ether residue is removed at an elevated temperature at water-pump pressure, 171 g. ethyl 2-allyloxy-6-nitrophenylpyruvate being obtained.

2-Allyloxy-6-nitrophenylacetic acid 171 g. Ethyl 2-allyloxy-6-nitrophenylpyruvate are oxidized in 1100 ml. 1 N aqueous sodium hydroxide solution with 6% hydrogen peroxide and the acid obtained is purified by dissolving in an aqueous solution of sodium bicarbonate, filtering and precipitating out with hydrochloric acid. After drying, there are obtained 88.5 g. 2-allyloxy-6-nitrophenylacetic acid; m.p. 115°–117° C. The yield is 74% of theory, referred to the 2-allyloxy-6-nitrotoluene.

Ethyl 2-allyloxy-6-nitrophenylacetate 23.7 g. 2-Allyloxy-6-nitrophenylacetic acid are converted into the ethyl ester with 17.4 ml. ethanol in toluene and 1.9 g. p-toluenesulphonic acid. After working up the reaction mixture, there are obtained 25.9 g. ethyl 2-allyloxy-6-nitrophenylacetate (97% of theory).

Ethyl 2-(2,3-epoxypropoxy)-6-nitrophenylacetate 10.6 g. Ethyl 2-allyloxy-6-nitrophenylacetate in 250 ml. chloroform are heated to the boil with 14.6 g. m-chloroperoxybenzoic acid until the reaction is complete. After working up in the usual manner, there are obtained 11 g. (99% of theory) ethyl 2-(2,3-epoxypropoxy)-6-nitrophenylacetate.

Ethyl 2-[2-hydroxy-3-(4-phenoxymethylpiperidino)-propoxy]-6-nitrophenylacetate 6.5 g. Ethyl 2-(2,3-epoxypropoxy)-6-nitrophenylacetate and 4.4 g. 4-phenoxymethylpiperidine are stirred in 65 ml. n-butanol for 18 hours at ambient temperature, then evaporated in a vacuum and the residue taken up with diethyl ether and 1 N lactic acid. The aqueous phase is rendered alkaline with an aqueous solution of potassium carbonate and extracted with diethyl ether. The ethereal phase is dried and evaporated to give 7.9 g. (72% of theory) ethyl 2-[2-hydroxy-3-(4-phenoxymethylpiperidino)-propoxy]-6-nitrophenylacetate in the form of a brownish oil.

The starting materials for the compounds of Examples (8a) to (8g) are obtained in an analogous manner:

| designation | Yield % | melting point °C. (solvent) |
|---|---|---|
| (for 8a) ethyl 2-{2-hydroxy-3-[4-(2-methoxyphenoxymethyl)-piperidino]-propoxy}-6-nitrophenylacetate from ethyl 2-(2,3-epoxypropoxy)-6-nitrophenylacetate and 4-(2-methoxyphenoxymethyl)-piperidine | 72 | oil |
| (for 8b) ethyl 2-{2-hydroxy-3-[4-(3-methylphenoxymethyl)-piperidino]-propoxy}-6-nitrophenylacetate from ethyl 2-(2,3-epoxypropoxy)-6-nitrophenylacetate and 4-(3-methylphenoxymethyl)-piperidine | 79 | oil |
| (for 8c) ethyl 2-{2-hydroxy-3-[4-(4-benzyloxyphenoxymethyl)-piperidino]-propoxy}-6-nitrophenylacetate from ethyl 2-(2,3-epoxypropoxy)-6-nitrophenylacetate and 4-(4-benzyloxyphenoxymethyl)-piperidine | 87 | oil |
| (for 8d) ethyl 2-{2-hydroxy-3-[4-(2-chlorophenoxymethyl)-piperidino]-propoxy}-6-nitrophenylacetate from ethyl 2-(2,3-epoxypropoxy)-6-nitrophenylacetate and 4-(2-chlorophenoxymethyl)-piperidine | 65 | oil |

-continued

| designation | Yield % | melting point °C. (solvent) |
|---|---|---|
| (for 8e) ethyl 2-{2-hydroxy-3-[4-(3-hydroxymethylphenoxymethyl)-piperidino]-propoxy}-6-nitrophenylacetate from ethyl 2-(2,3-epoxypropoxy)-6-nitrophenylacetate and 4-(3-hydroxymethylphenoxymethyl)-piperidine | 80 | oil |
| (for 8f) ethyl 2-{2-hydroxy-3-[4-(2-methyl-6-pyridoxymethyl)-piperidine]-propoxy}-6-nitrophenylacetate from ehtyl 2-(2,3-epoxypropoxy)-6-nitrophenylacetate and 4-(2-methyl-6-pyridoxymethyl)-piperidine | 99 | oil |
| (for 8g) ethyl 2-{2-hydroxy-3-[4-(4-aminocarbonyl-methylphenoxymethyl)-piperidino]-propoxy}-6-nitrophenylacetate from ethyl 2-(2,3-epoxypropoxy)-6-nitrophenylacetate and 4-(4-aminocarbonylmethylphenoxymethyl)-piperidine | 95 | oil |

EXAMPLE 9

4-{2-Hydroxy-3-[4-(2-pyridyloxymethyl)-piperidino]-propoxy}-indazole

A mixture of 5.6 g. 2-benzyl-4-(2,3-epoxypropoxy)-indazole, 3.9 g. 4-(2-pyridyloxymethyl)-piperidine and 5 ml. 1,2-dimethoxyethane is heated to 70° C. for 20 hours. Subsequently, the reaction mixture is evaporated, the residue is taken up in 120 ml. methanol, 10 ml. concentrated hydrochloric acid are added thereto and the reaction mixture then hydrogenated in the presence of palladium-charcoal (10%) at atmospheric pressure. After filtering off the catalyst with suction, the filtrate is evaporated and the residue is dissolved in water, rendered alkaline with an aqueous solution of sodium hydroxide and extracted with dichloromethane. After drying the extract with anhydrous sodium sulphate and evaporating, there is obtained an oil which is triturated with diethyl ether, followed by recrystallization from ethyl acetate, using active charcoal, to give 3.9 g. (51% of theory) 4-{2-hydroxy-3-[4-(2-pyridyloxymethyl)-piperidino]-propoxy}-indazole; m.p. 81°–83° C.

The 2-benzyl-4-(2,3-epoxypropoxy)-indazole used as starting material can be obtained as follows:

9.2 g. Sodium hydride (55–60% suspension in paraffin) is introduced, with cooling and under an atmosphere of nitrogen, into a solution of 47.1 g. 2-benzyl-4-hydroxyindazole in 250 ml. dimethylformamide. When the evolution of hydrogen has ceased, 19 ml. epibromohydrin are added dropwise thereto and the reaction mixture stirred for 16 hours at ambient temperature. The reaction mixture is then poured into 1.5 liters water, extracted with dichloromethane and the extract evaporated to give an oil which is purified over a column of silica gel, using dichloromethane/methanol (99:1 v/v) as elution agent. From the evaporation residue of the initial fractions, there are obtained, by trituration with ligroin-diethyl ether (1:1 v/v), 30.0 g. (51% of theory) 2-benzyl-4-(2,3-epoxypropoxy)-indazole in the form of colorless crystals; m.p. 66°–68° C.

In an analogous manner, by reacting 2-benzyl-4-(2,3-epoxypropoxy)-indazole with 4-(4-benzimidazolinonyloxymethyl)-piperidine, followed by hydrogenation, there is obtained, in a yield of 44% of theory, 4-{2-hydroxy-3-[4-2-benzimidazolinonyloxymethyl)-piperidino]-propoxy}-indazole; m.p. 253°–255° C.

EXAMPLE 10

4-[2-Hydroxy-3-(4-phenoxymethylpiperidino)-propoxy]-carbazole hydrochloride 4.3 g. 4-Phenoxymethylpiperidine and 5.35 g. 4-(2,3-epoxypropoxy)-carbazole are heated to 120° C. for 4 hours. After cooling, the reaction mixture is dissolved in acetone and mixed with ethereal hydrochloric acid. The precipitated hydrochloride is filtered off with suction and recrystallized from isopropanol/ethanol to give 8.0 g. (69% of theory) 4-[2-hydroxy-3-(4-phenoxymethylpiperidino)-propoxy]-carbazole hydrochloride; m.p. 224°–225° C.

The following compounds are obtained in an analogous manner from 4-(2,3-epoxypropoxy)-carbazole and the appropriately substituted 4-methylpiperidine derivatives:

| | designation | yield % of theory | melting point °C. (solvent) |
|---|---|---|---|
| (a) | 4-{2-hydroxy-3-[4-(2-chlorophenoxymethyl)-piperidino]-propoxy}-carbazole hydrochloride | 61 | 213–215 (ethanol/methanol) |
| (b) | 4-{2-hydroxy-3-[4-(2-methoxyphenoxymethyl)-piperidino]-propoxy}-carbazole hydrochloride | 65 | 180 (decomp.) (ethanol/methanol) |
| (c) | 4-{2-hydroxy-3-[4-(2-methylphenoxymethyl)-piperidino]-propoxy}-carbazole hydrochloride | 83 | 150 (decomp.) (acetone) |
| (d) | 4-{2-hydroxy-3-[4-(3-methylphenoxymethyl)-piperidino]-propoxy}-carbazole hydrochloride | 74 | 212–215 (acetone) |
| (e) | 4-{2-hydroxy-3-[4-(2-pyridyloxymethyl)-piperidino]-propoxy}-carbazole hydrochloride | 50 | 180–182 (ethanol) |

EXAMPLE 11

4-{2-Hydroxy-3-[4-(4-2-benzimidazolinonyloxymethyl)-piperidino]-propoxy}-carbazole hydrochloride 3.6 g. 4-(2,3-Epoxypropoxy)-carbazole and 3.7 g. 4-(4-2-benzimidazolinonyloxymethyl)-piperidine are heated under reflux for 20 hours in 75 ml. ethanol and 10 ml. water. The reaction mixture is then evaporated and the residue chromatographed over a column of silica gel, using dichloromethane/methanol (80:20 v/v) as elution agent. The eluate is evaporated and the residue taken up in tetrahydrofuran, from which the hydrochloride is precipitated by the addition of tetrahydrofuran/hydrochloric acid. There are obtained 3.1 g. (43% of theory) 4-{2-hydroxy-3-[4-(4-2-benzimidazolinonyloxymethyl)-piperidino]-propoxy}-carbazole hydrochloride; m.p. 185° C. (decomp.).

EXAMPLE 12

4-{2-Hydroxy-3-[4-(4-2-benzimidazolinonyloxymethyl)-piperidino]-propoxy}-6-methylbenzotriazole hydrochloride 7.7 g. 2,3-Diamino-1-{2-hydroxy-3-[4-(4-2-benzimidazolinonyloxymethyl)-piperidino]-propoxy}-5-methylbenzene trihydrochloride are dissolved in 45 ml. water and 17 ml. glacial acetic acid. The solution is cooled to 0° C., mixed with 1.0 g. sodium nitrite in 1.6 ml. water and then stirred for 1 hour at ambient temperature. The solid precipitate is isolated and recrystallized from ethanol/ethyl acetate. There are obtained 3.4 g. (50% of theory) 4-{2-hydroxy-3-[4-(4-2-benzimidazolinonyloxymethyl)-piperidino]-propoxy}-6-methylbenzotriazole hydrochloride; m.p. 227°–230° C.

The diamino compound used as starting material is obtained in the following manner:

6.72 g. 2-(2,3-Epoxypropoxy)-4-methyl-6-nitroaniline and 7.10 g. 4-2-benzimidazolinonyloxymethyl-piperidine are boiled under reflux for 8 hours in 200 ml. ethanol. The reaction mixture is then introduced into 100 ml. ethanol containing 0.3 g. platinum dioxide and hydrogenated at ambient temperature and atmospheric pressure. The reaction mixture is filtered and the filtrate is acidified with ethereal hydrochloric acid, followed by suction filtration to give 7.7 g. 2,3-diamino-1-{2-hydroxy-3-[4-(4-2-benzimidazolinonyloxymethyl)-piperidino]-propoxy}-5-methylbenzene trihydrochloride.

EXAMPLE 13

4-{2-Hydroxy-3-[4-(2-pyridyloxymethyl)-piperidino]-propoxy}-7-methylbenzimidazole hydrochloride 18.0 g. 2,3-Diamino-1-{2-hydroxy-3-[4-(2-pyridyloxymethyl)-piperidino]-propoxy}-4-methylbenzene trihydrochloride are boiled under reflux for 2 hours in 60 ml. formic acid. The formic acid is then completely distilled off and the residue is boiled for 2 hours in 60 ml. 2 N hydrochloric acid, clarified with active charcoal and, after filtering, evaporated to dryness. The residue is recrystallized from 160 ml. ethanol/40 ml. methanol to give 8.5 g. (54% of theory) 4-{2-hydroxy-3-[4-(2-pyridyloxymethyl)-piperidino]-propoxy}-7-methylbenzimidazole hydrochloride; m.p. 188°–190° C.

EXAMPLE 14

4-{2-Hydroxy-3-[4-(2-pyridyloxymethyl)-piperidino]-propoxy}-2-methylbenzimidazole hydrochloride 9.6 g. 2,3-Diamino-1-{2-hydroxy-3-[4-(2-pyridyloxymethyl)-piperidino]-propoxy}-benzene trihydrochloride are boiled for 3 hours in 50 ml. glacial acetic acid. After evaporating to dryness, the partly resulting 2-0-acetyl compound is saponified in 50 ml. 2 N hydrochloric acid by boiling under reflux for 2 hours. After clarifying with active charcoal, the solution is evaporated and the residue recrystallized from ethanol/ethyl acetate. There are obtained 2.3 g. (27% of theory) 4-{2-hydroxy-3-[4-(2-pyridyloxymethyl)-piperidino]-propoxy}-2-methylbenzimidazole hydrochloride; m.p. 166°–169° C.

EXAMPLE 15

4-{2-Hydroxy-3-[4-(2-butoxyphenoxymethyl)-piperidino]-propoxy}-1-formylindoline p-chlorobenzoate A solution of 2.2 g. 4-(2,3-epoxypropoxy)-1-formylindoline and 2.6 g. 4-(2-butoxyphenoxymethyl)-piperidine in 50 ml. n-butanol is stirred for 18 hours, then evaporated and the residue dissolved in ethyl acetate, whereafter an equivalent amount of p-chlorobenzoic acid is added thereto. The precipitate obtained is filtered off with suction and recrystallized from ethyl acetate to give 3.3 g. (51% of theory) 4-{2-hydroxy-3-[4-(2-n-butoxyphenoxymethyl)-piperidino]-propoxy}-1-formylindoline p-chlorobenzoate; m.p. 110°–113° C.

The following compounds are obtained in an analogous manner:

| designation | yield % of theory | melting point °C. (solvent) |
|---|---|---|
| (a) 4-{2-hydroxy-3-[4-(3,4-methylenedioxyphenoxymethyl)-piperidino]-propoxy}-1-formylindoline from 4-(2,3-epoxypropoxy)-1-formylindoline and 4-(3,4-methylenedioxyphenoxymethyl)-piperidine | 59 | 130–132 (isopropanol) |
| (b) 4-{2-hydroxy-3-[4-(4-aminophenoxymethyl)-piperidino]-propoxy}-1-formylindoline from 4-(2,3-epoxypropoxy)-1-formylindoline and 4-(4-aminophenoxymethyl)-piperidine | 25 | 75 |
| (c) 4-{2-hydroxy-3-[4-(4-acetamidophenoxymethyl)-piperidino]-propoxy}-1-formylindoline from 4-(2,3-epoxypropoxy)-1-formylindoline and 4-(4-acetamidophenoxymethyl)-piperidine | 67 | 178–180 (butanol) |
| (d) 4-{2-hydroxy-3-[4-(4-methanesulphonylamidophenoxymethyl)-piperidino]-propoxy}-1-formylindoline from 4-(2,3-epoxypropoxy)-1-formylindoline and 4-(4-methanesulphonylamidophenoxymethyl)-piperidine | 25 | 127–128 (methanol) |

The 4-(2,3-epoxypropoxy)-1-formylindoline required as starting material for the preparation of the above compound is obtained in the following manner:

200 ml. 1 N Potassium tert.-butylate solution is added dropwise to 48.6 g. 2-benzyloxy-6-nitrotoluene and 29.9 g. paraformaldehyde dissolved in 670 ml. dimethylformamide. After stirring for 1 hour at ambient temperature, the reaction mixture is stirred into 3 liters ice water and extracted with diethyl ether. The ethereal phase is dried with anhydrous sodium sulphate and evaporated in a vacuum to give 62 g. 2-benzyloxy-6-nitrophenylethanol which, as crude product, is used in the next stage.

62.0 g. 2-Benzyloxy-6-nitrophenylethanol are dissolved in 500 ml. anhydrous pyridine and, while cooling to about 10° C., mixed with 47.7 g. p-toluenesulphonyl chloride. The reaction mixture is allowed to warm up to ambient temperature and then stirred for about 10 hours until the reaction is complete, whereafter the reaction mixture is stirred into ice water. The precipitate obtained is filtered off with suction, washed with water and dried to give 74 g. (86% of theory) 2-(2-benzyloxy-6-nitrophenyl)-ethyl p-toluenesulphonate; m.p. 96°–98° C.

74 g. 2-(2-Benzyloxy-6-nitrophenyl)-ethyl p-toluenesulphonate are dissolved in 2 liters ethylene glycol monomethyl ether, mixed with 5 g. 10% palladium-active charcoal and hydrogenated at ambient temperature and 1 bar hydrogen pressure. After filtering off the catalyst, the filtrate is evaporated and the residue formylated with a mixture of 227 ml. acetic anhydride and 91 ml. formic acid (according to the method of C. W. Huffmann, J. org. Chem., 23, 727/1958). After the reaction is complete, the reaction mixture is mixed with ice water and extracted with ethyl acetate. The organic phase is neutralized, dried with anhydrous sodium sulphate and evaporated in a vacuum. The residue obtained is mixed with 320 ml. epichlorohydrin and 173 ml. 2 N sodium methylate solution added thereto. After stirring overnight, the reaction mixture is evaporated and the residue dissolved in water and ethyl acetate. From the ethyl acetate evaporation residue, there are obtained, by trituration with isopropanol and filtering off with suction, 15.8 g. (42% of theory) 4-(2,3-epoxypropoxy)-1-formylindoline; m.p. 88°–89° C.

EXAMPLE 16

4-{2-Hydroxy-3-[4-(4-acetamidophenoxymethyl)-piperidino]-propoxy}-1-formylindoline 3.3 g. 4-{2-Hydroxy-3-[4-(4-aminophenoxymethyl)-piperidino]-propoxy}-1-formylindoline (preparation see Example 15b) are stirred with a mixture of 25 ml. acetic anhydride and 25 ml. pyridine for 10 hours at ambient temperature, then evaporated in a vacuum and the residue dissolved in water and dichloromethane. After neutralization with sodium bicarbonate, the organic phase is distilled and the residue obtained is converted in methanol with sodium methylate solution into the desired compound. By shaking out between dichloromethane and water and evaporating the organic phase, there is obtained 1.0 g. (27% of theory) 4-{2-hydroxy-3-[4-(4-acetamidophenoxymethyl)-piperidino]-propoxy}-1-formylindoline; m.p. 177°–179° C.

The following compound is obtained in an analogous manner:

| designation | yield % of theory | melting point °C. (solvent) |
| --- | --- | --- |
| (a) 4-{2-hydroxy-3-[4-(4-methanesulphonylamidophenoxymethyl)-piperidino[-propoxy}-1-formylindoline from 4-{2-hydroxy-3-[4-(4-aminophenoxymethyl)-piperidino]-propoxy}-1-formylindoline and methanesulphonic acid chloride | | |

EXAMPLE 17

4-[3-(4-Phenoxymethylpiperidino)-propoxy]-carbazole 4.6 g. 4-hydroxycarbazole are added to a solution of 0.55 g. sodium in 100 ml. isopropanol, heated under reflux, cooled to ambient temperature and 6.9 g. 3-(4-phenoxymethylpiperidino)-propyl chloride (see U.S. Pat. No. 4,086,347) added thereto, followed by boiling under reflux for 5 hours. The reaction mixture is then evaporated and the residue is taken up in dilute aqueous sodium hydroxide solution, extracted with diethyl ether and the extract evaporated. After recrystallizing the residue from isopropanol/ligroin, there are obtained 4.7 g. (46% of theory) 4-[3-(4-phenoxymethylpiperidino)-propoxy]-carbazole; m.p. 126°–128° C.

EXAMPLE 18

In a manner analogous to that described in Example 15, there are obtained the following compounds:

| designation | yield % of theory | melting point °C. (solvent) |
| --- | --- | --- |
| (a) 4-{2-hydroxy-3-[4-(2-pyridyloxymethyl)-piperidino]-propoxy}-indole benzoate from 4-(2,3-epoxypropoxy)-indole and 4-(2-pyridyloxymethyl)-piperidine | 45 | 117–119 (isopropanol) |
| (b) 4-{2-hydroxy-3-[4-(3,4-methylenedioxyphenoxymethyl)-piperidino]-propoxy}-indole benzoate from 4-(2,3-epoxypropoxy)-indole and 4-(3,4-methylenedioxyphenoxymethyl)-piperidine | 72 | 148–150 (ethyl acetate) |
| (c) 4-{2-hydroxy-3-[4-(4-2-benzimidazolinonyloxymethyl)-piperidino]-propoxy}-indole acetate from 4-(2,3-epoxypropoxy)-indole and 4-(4-2-benzimidazolinonyloxymethyl)-piperidine | 52 | 208–210 (butanol) |
| (d) 4-{2-hydroxy-3-[4-(4-2-benzimidazolinonyloxymethyl)-piperidino]-propoxy}-2-hydroxymethylindole acetate from 4-(2,3-epoxypropoxy)-2-hydroxymethylindole and 4-(4-2-benzimidazolinonyloxymethyl)-piperidine | 58 | 174–178 (ethanol) |
| (e) 4-{2-hydroxy-3-[4-(2-pyridyloxymethyl)-piperidino]-propoxy}-2-hydroxymethylindole benzoate from 4-(2,3-epoxypropoxy)-2-hydroxymethylindole and 4-(2-pyridyloxymethyl)-piperidine | 55 | 76–78 (isopropanol) |
| (f) 4-{2-hydroxy-3-[4-(2-pyridyloxymethyl)-piperidino]-propoxy}-2-ethoxycarbonylindole from 4-(2,3-epoxypropoxy)-2-ethoxycarbonylindole and 4-(2-pyridyloxymethyl)-piperidine | 51 | 154–156 (isopropanol) |
| (g) 4-{2-hydroxy-3-[4-(3-acetyl-4-hydroxyphenoxymethyl)-piperdino]-propoxy}-indole from 4-(2,3-epoxypropoxy)-indole and 4-(3-acetyl-4-hydroxyphenoxymethyl)-piperidine | 21 | 148–149 (diethyl ether) |

EXAMPLE 19

4-{2-Hydroxy-3-[4-(2-pyridyloxymethyl)-piperidino]-propoxy}-2-hydroxymethylindole benzoate.

A solution of 4.6 g. 4-{2-hydroxy-3-[4-(2-pyridyloxymethyl)-piperidino]-propoxy}-2-ethoxycarbonylindole (preparation see Example 18f) in 125 ml. anhydrous tetrahydrofuran is added dropwise to a suspension of 1 g. lithium aluminum hydride in 125 ml. anhydrous tetrahydrofuran. The reaction mixture is then stirred for 30 minutes, decomposed, while cooling, with an aqueous solution of sodium chloride and 10 N aqueous sodium hydroxide solution, filtered, washed with tetrahydrofuran and evaporated. By adding an equivalent amount of benzoic acid, there are obtained 4.0 g. (74% of theory) 4-{2-hydroxy-3-[4-(2-pyridyloxymethyl)-piperidino]-propoxy}-2-hydroxymethylindole benzoate which is recrystallized from isopropanol; m.p. 76°–78° C.

EXAMPLE 20

4-{2-Benzoyloxy-3-[4-(2-pyridyloxymethyl)-piperidino]-propoxy}-7-methylbenzimidazole hydrochloride 4.87 g. 4-{2-Hydroxy-3-[4-(2-pyridyloxymethyl)-piperidino]-propoxy}-7-methylbenzimidazole (preparation see Example 13), 19.5 g. benzoic acid and 2.12 g. benzoic anhydride are heated under reflux for 2 hours in 100 ml. benzene and 25 ml. dimethylformamide. After removing the solvent, the residue is taken up in 100 ml. water, rendered alkaline with concentrated aqueous ammonia solution and extracted with chloroform. The chloroform phase is washed with water, dried over anhydrous sodium sulphate and evaporated. The residue is taken up in ethanol and mixed with ethereal hydrochloric acid. After adding isopropanol and diethyl ether, there crystallize out 2.1 g. (41% of theory) 4-{2-benzoyloxy-3-[4-(2-pyridyloxymethyl)-piperidino]-propoxy}-7-methylbenzimidazole hydrochloride; m.p. 178°–181° C.

EXAMPLE 21

Tablets are prepared, each of which contains 10 mg. 4-[2-hydroxy-3-(4-phenoxymethylpiperidino)-propoxy]-2-benzimidazolinone. The tablets are produced according to the following formulation:

4-[2-hydroxy-3-(4-phenoxymethylpiperidine)-propoxy]-2-benzimidazolinone: 10 g.
lactose: 80 g.
starch: 29 g.
magnesium stearate: 1 g.

The active compound is fully powdered and mixed with the lactose and starch and the mixture is granulated in conventional manner. The magnesium stearate is added to the granulate and the mixture used for pressing 1000 tablets, each of which has a weight of 0.12 g.

Test Report

The new compounds were tested in regard to their vasodilating and β-blocking activity, comparing them to the 4-[2-hydroxy-3-(4-phenyloxymethylpiperidino)-propoxy]-indole from U.S. Pat. No. 4,146,630. Since the two properties cannot be examined in a single test mode, different test arrangements had to be used.

(a) Testing for vasodilating activity

Vasodilation manifests itself by a lowering of blood pressure. Rabbits were anesthetized with urethane. A catheter was implanted in the A. femoralis for a continuous measurement of the arterial blood pressure. Measurement of the blood pressure was effected by means of an electromechanical transducer (Statham P 23 Db).

The pulse beats were registered on a direct printer and evaluated after calibration with a mercury manometer.

After determining the starting value, the two carotid arteries (A. carotis) were occluded for 2 min. and the blood pressure thus temporarily raised (CSE Reflex). Following that, the test substance was intravenously injected in the lowest dose (0.125 mg/kg) and another 8 min. later, in logarithmithically rising dosages (factor 2), the test substances were injected again and the CSE released again (dosages: 0.125, 0.125, 0.25, 1.0 . . . mg/kg).

Substances which under these conditions weaken the rise of blood pressure under CSE can be regarded as vasodilating. From the test substances, the dose which weakens the CSE reflex by 30 mm Hg ($ED_{-30\ mm\ Hg}$) was calculated.

Since in each test the dosage was increased until the animal died of toxic symptoms the fatal dose (lethal dose, LD) could thus be determined for each animal. From the individual quotient $LD:ED_{-30\ mm\ Hg}$ the therapeutic index can then be calculated.

In several cases, the lethal dose could not be determined since the solubility limit was lower than the tolerance limit (this is indicated in the table by the symbol >).

(b) Testing for β-blocking activity

Rabbits were fixed in wooden cages, and the heart beat frequency derived via electrodes and read off on a frequency counter (measuring time 15 sec.). Over an ear vein, 1 μg/kg isoprenaline was first intravenously injected, causing an increase of the heartbeat frequency from about 200 beats/min to 330 beats/min. Following that, the test substances were administered intravenously in increasing dosages (see method a) and the heart beat frequency after isoprenaline counted out again. The retardation of the isoprenaline tachycardia can be regarded as β-blocking. The dose of test substances that limits the rise of the isoprenaline tachycardia by half ($HD_{50}\%$) was determined.

The data from the two tests are given in the table. The equieffective doses ($DE_{-30\ mm\ Hg}$, $HD_{50}\%$, LD) as well as the quotient were calculated logarithmically from 4–6 individual tests.

| Active material | β-BLOCKING AND VASO-DILATING ACTIVITY | | | |
|---|---|---|---|---|
| | $DE_{-30\ mm\ Hg}$ (vasodilating activity (μg/kg i.v.) | $HD_{50}\%$ (β-blocking Activity (μg/kg i.v.) | LD (toxic dose) (μg/kg i.v.) | $\dfrac{LD}{ED_{-30\ mm\ Hg}}$ (individual log. calculated) |
| A* | 1120 | 1673 | 16130 | 13 |
| Example (1a) | 880 | 1156 | 16000 | 18 |

-continued

β-BLOCKING AND VASO-DILATING ACTIVITY

| Active material | $DE_{-30\ mm\ Hg}$ (vasodilating activity) (μg/kg i.v.) | $HD_{50\%}$ (β-blocking Activity) (μg/kg i.v.) | LD (toxic dose) (μg/kg i.v.) | $\frac{LD}{ED_{-30\ mm\ Hg}}$ (individual log. calculated) |
|---|---|---|---|---|
| Example (1b) | 300 | 866 | 56570 | 19 |
| Example (1f) | 1520 | 885 | >32000 | >21 |
| Example (1g) | 920 | 171 | >11200 | >12 |
| Example (4a) | 240 | 1018 | >26000 | >106 |
| Example (8b) | 2370 | 360 | 32000 | 13 |
| Example (8c) | 418 | 829 | 20159 | 48 |
| Example (10b) | 1600 | 217 | >10763 | >7 |
| Example (10c) | 780 | 1031 | 16127 | 21 |
| Example (10d) | 950 | 368 | 12800 | 14 |

*A [2-Hydroxy-3-(4-phenoxymethyl-piperidino)-propoxyl] -indole from U.S. Pat. No. 4,146,630.

It will be appreciated that the instant specification and examples are set forth by ways of illustration and not limitation, and that various modifications and changes may be made without departing from the spirit and scope of the present invention.

We claim:

1. A piperidinopropyl derivative of the formula in which
  $R_1$ and $R_2$ each independently is hydrogen or a lower alkyl radical, or together are a $C_{2-4}$-alkylene radical,
  $R_3$ is hydrogen, hydroxy, or lower alkanoyloxy,
  $R_4$ is hydrogen or formyl,
  A is (a) —$X_1$=$Y_1$ in which
    (i) $X_1$ and $Y_1$ each independently is a nitrogen atom or —C($R_6$)=, in which
    (A)$R_6$ is hydrogen, a lower alkyl radical optionally substituted by hydroxy or lower alkanoyloxy, a carboxyl radical or an alkoxycarbonyl radical, or
  (b)—$X_2$—$Y_2$ in which
    (i) $X_2$ is —$CH_2$— or —N($R_7$)—, in which (A)$R_7$ is hydrogen or lower alkyl, and
    (ii) $Y_2$ is —$CH_2$— or —C(=Z)—, in which (A)Z is oxygen or sulfur, or
  (c)—$CR_8$=$CR_9$— in which
    (i) $R_8$ and $R_9$ together are a —CH=CH—CH=CH—bridge, with the proviso that when present, it is $Y_1$ or $Y_2$ which is connected to N—$R_4$, and
  B is a pyridyl, primidyl, benzimidazolinyl, benzimidazolinyl, benztriazolyl, indazolyl, benzodioxolanyl or carbazolyl radical or, if A is —$X_2$—$Y_2$— or —$CR_8$=$CR_9$, may also be a phenyl radical, either of which is optionally substituted by halogen, hydroxyl, lower alkyl, hydroxy-lower alkyl, carboxamido-lower alkyl, lower alkoxy, amino, carboxamido, lower alkyl-carbonylamino, lower alkanoyloxy or lower alkylsulphonylamino,
or a pharmacologically acceptable salt thereof.

2. A compound or salt according to claim 1, in which $R_1$ and $R_2$ each independently is hydrogen or $C_{1-4}$-alkyl, or together are $C_{2-4}$-alkylene,
$R_3$ is hydrogen, hydroxy, or $C_{2-6}$-alkanoyloxy or benzoyloxy optionally substituted by halogen, lower alkyl or lower alkoxy,
A together with the adjacent benzene ring and >N—$R_4$ forms a benzimidazolin-2-one, benzimidazoline-2-thione, oxindole, indazole, carbazole, benztriazole, benzimidazole, indoline or indole moiety, and
B is a pyridyl, pyrimidyl, benzimidazolinonyl, or benzodioxolanyl radical or, if A is —$X_2$—$Y_2$— or —$CR_8$=$CR_9$—, may also be a phenyl radical, any of which is optionally substituted by halogen, hydroxy, $C_{1-4}$-alkyl, hydroxy-$C_{1-4}$-alkyl, carboxamido-$C_{1-4}$, $C_{1-4}$-alkoxy, amino, carboxamido, $C_{1-4}$-alkylcarbonylamino, $C_{2-6}$-alkanoyl or $C_{1-4}$-alkylsulphonylamino.

3. A compound or salt according to claim 1, in which said compound is 4-{2-hydroxy-3-[4-(2-methoxyphenoxymethyl)-piperidino]-propoxy}-2-benzimidazolinone hydrochloride.

4. A compound or salt according to claim 1, in which said compound is 4-{2-hydroxy-3-[4-(3-methylphenoxymethyl)-piperidino]-propoxy}-2-benzimidazoline.

5. A compound or salt according to claim 1, in which said compound is 4-{2-hydroxy-3-[4-(4-2-benzimidazolinonyloxymethyl)-piperidino]-propoxy}-2-benzimidazolinone.

6. A compound or salt according to claim 1, in which said compound is 4-{2-hydroxy-3-[4-(4-hydroxyphenoxymethyl)-piperidino]-propoxy}-oxindole acetate.

7. A compound or salt according to claim 1, in which said compound is 4-{2-hydroxy-3-[4-(3-methylphenoxymethyl)-piperidino]-propoxy}-carbazole.

8. An andrenergic β-receptor-inhibitory and blood pressure lowering composition of matter comprising an adrenergic β-receptor-inhibiting or blood pressure lowering effective amount of a compound or salt according to claim 1 in admixture with a pharmacologically acceptable diluent.

9. A method of inhibiting adrenergic β-receptors and lowering blood pressure in a patient which comprises administering to such patient an adrenergic β-receptor-inhibiting or blood pressure lowering effective amount of a compound or salt according to claim 1.

10. The method according to claim 9 in which said compound is
  4-{2-hydroxy-3-[4-(2-methoxy-phenoxymethyl)-piperidino]-propoxy}-2-benzimidazolinone hydrochloride,
  4-{2-hydroxy-3-[4-(3-methylphenoxymethyl)-piperidino]-propoxy}-2-benzimidazolinone, 4-{2-hydroxy-3-[4-(4-2-benzimidazolinonyloxymethyl)-piperidino]-propoxy}-2-benzimidazolinone,
4-{2-hydroxy-3-[4-(4-hydroxyphenoxymethyl)-piperidino]-propoxy}-oxindole acetate,
4-{2-hydroxy-3-[4-(3-methylphenoxymethyl)-piperidino]-propoxy}-carbazole, or
a pharmacologically acceptable salt thereof.

* * * * *